(12) United States Patent
Wood et al.

(10) Patent No.: US 8,137,415 B2
(45) Date of Patent: Mar. 20, 2012

(54) COLORING COMPOSITION

(75) Inventors: Jonathan Wood, Weinheim (DE);
Alexandra Meuser, Weinheim (DE);
Mustafa Grit, Gernsheim (DE)

(73) Assignee: KPSS KAO Professional Salon Services GmbH, Darmstadt (DE)

( * ) Notice: Subject to any disclaimer, the term of this patent is extended or adjusted under 35 U.S.C. 154(b) by 0 days.

(21) Appl. No.: 13/124,096

(22) PCT Filed: Oct. 20, 2009

(86) PCT No.: PCT/EP2009/007500
§ 371 (c)(1),
(2), (4) Date: Apr. 13, 2011

(87) PCT Pub. No.: WO2010/046078
PCT Pub. Date: Apr. 29, 2010

(65) Prior Publication Data
US 2011/0197911 A1 Aug. 18, 2011

(30) Foreign Application Priority Data
Oct. 20, 2008 (EP) ................................... 08018285

(51) Int. Cl.
*A61Q 5/10* (2006.01)

(52) U.S. Cl. ............. 8/405; 8/407; 8/408; 8/426; 8/435; 8/552; 8/581; 8/632

(58) Field of Classification Search ............... 8/405, 407, 8/408, 426, 435, 552, 581, 632
See application file for complete search history.

(56) References Cited

U.S. PATENT DOCUMENTS

| 6,451,298 B1 | 9/2002 | Decoster |
| 2003/0028979 A1* | 2/2003 | Duffer et al. ...................... 8/406 |
| 2004/0126349 A1 | 7/2004 | Anderson |
| 2007/0041929 A1 | 2/2007 | Torgerson |

FOREIGN PATENT DOCUMENTS

| EP | 0 874 017 A2 | 10/1998 |
| EP | 1 232 741 A1 | 8/2002 |
| EP | 1 676 567 A1 | 8/2002 |
| EP | 1 797 861 A1 | 6/2007 |
| EP | 1 894 556 A2 | 3/2008 |
| EP | 1 897 532 A1 | 3/2008 |
| GB | 2 385 056 A | 8/2003 |
| WO | 2007/102792 A1 | 9/2007 |

OTHER PUBLICATIONS

International Search Report Dated May 7, 2010.

* cited by examiner

*Primary Examiner* — Eisa Elhilo
(74) *Attorney, Agent, or Firm* — Norris McLaughlin & Marcus PA

(57) ABSTRACT

The present invention is related to an aqueous composition comprising an alkalizing agent and an aqueous emulsion of a silicone copolymer. The inventors of the present invention have surprisingly found out that a composition comprising at least one alkalizing agent and an aqueous emulsion of divinyldimethicone/dimethicone copolymer with an internal phase viscosity of more than $1 \times 10^8$ mm$^2$/s measured at 0.01 Hz and at about 25° C. colors and/or permanently shapes hair excellently and improves hair shine, combability and manageability and especially hair treated with such composition has less flyaway. Additionally it has been observed that hair colored and/or permanently shaped more homogeneously from root to tips. The subject of the present invention is an aqueous composition for human hair comprising at least one alkalizing agent and an aqueous emulsion of divinyldimethicone/dimethicone copolymer with an internal phase viscosity of more than $1 \times 10^8$ mm$^2$/s measured at 0.01 Hz and at about 25° C.

15 Claims, No Drawings

COLORING COMPOSITION

This application is a 371 application of PCT/EP2009/007500 filed Oct. 20, 2009, which claims foreign priority benefit under 35 U.S.C. §119 of European Application No. 0801825.0 filed Oct. 20, 2008.

The present invention is related to an aqueous composition comprising an alkalizing agent and an aqueous emulsion of a silicone copolymer.

Alkaline compositions have been used in various fields of hair dressing such as hair colouring and/or permanent shaping. Alkaline pH's are preferred because the reaction speed is higher at this pH range so that the hair dressing service can be carried out in a short period of time. On the other hand, alkaline pH values are learned to be damaging human hair so that especially after repeated application hair looses its natural like character and needs to be "repaired" by using so called repairing agents which may be highly costly and time consuming to the consumers.

The colourations are divided into two main groups, the first being permanent colouration based on mainly oxidative hair dyes which penetrate into hair and polymerize, and the second is based on direct dyes which is, without excluding any penetration, mainly adsorbed onto hair and widely based on cationic and neutral dyes. In the latter, recently compositions based on anionic direct dyes have also been made available by the applicant which deliver brilliant, shiny and long lasting colours.

The other area where alkaline agents are preferred is permanent shaping of hair and it is based on reducing disulfide bonds in hair fibres with a reducing agent comprising composition and reoxidizing them again in a new shape.

It has been observed that with the use of both hair colouring and permanent shaping hair is damaged so that it is difficult to comb, hair looses its natural elasticity, natural volume and body and quite importantly, its natural shine. It has to be noted that especially after a permanent shaping, hair is less shiny. Therefore, there is a great need for improved products which either does not result in less shiny hair or at least loss of shine is not that high so that hair has still attractive appearance.

The present invention starts with the above mentioned problems of hair shine, unsatisfactory hair condition after use of alkaline composition especially oxidative hair colouration and permanent shaping and aims at providing an alkaline composition for hair which does not show at least one of the above mentioned disadvantages.

The inventors of the present invention have surprisingly found out that a composition comprising at least one alkalizing agent and an aqueous emulsion of divinyldimethicone/dimethicone copolymer with an internal phase viscosity of more than $1 \times 10^8$ mm$^2$/s measured at 0.01 Hz and at about 25° C. colours and/or permanently shapes hair excellently and improves hair shine, combability and manageability and especially hair treated with such composition has less flyaway. Additionally it has been observed that hair coloured and/or permanently shaped more homogeneously from root to tips.

Accordingly, the subject of the present invention is an aqueous composition for human hair comprising at least one alkalizing agent and an aqueous emulsion of divinyldimethicone/dimethicone copolymer with an internal phase viscosity of more than $1 \times 10^8$ mm$^2$/s measured at 0.01 Hz and at about 25° C.

Aqueous composition of the present invention comprise aqueous emulsion of divinyldimethicone/dimethicone copolymer with a viscosity of more than $1 \times 10^8$ mm$^2$/s, preferably $1.1 \times 10^8$ mm$^2$/s, and more preferably $1.2 \times 10^8$ mm$^2$/s.

Divinyldimethicone/dimethicone copolymer is comprised in compositions of the present invention at a concentration of 0.01 to 5% by weight, preferably 0.02 to 3%, more preferably 0.05 to 2.5% by weight and most preferably 0.1 to 1.5% by weight calculated to total composition as Divinyldimethicone/dimethicone copolymer.

In a preferred embodiment of the present invention, aqueous divinyldimethicone/dimethicone copolymer emulsion comprises non-ionic surfactants and dispersed droplet has an average droplet size of smaller than 0.6 µm. Suitable divinyldimethicone/dimethicone copolymer emulsion with an internal phase viscosity at 0.01 Hz more than $1.2 \times 108$ is available from Dow Corning under the trade name HMW 2220. The non-ionic emulsion comprises C12-13 Pareth-23 and C12-13 Pareth-3 as non-ionic emulsifiers.

All concentration mentioned within the description refers to the concentration of the respective compound in the composition prior to mixing with any other composition, if necessary, unless otherwise mentioned.

Composition of the present invention comprises at least one alkalizing agent. Concentration of at least one alkalizing agent is in the range of 0.1 to 30%, preferably 0.35 to 25%, more preferably 0.5 and 20% and most preferably 1 and 15% by weight, calculated to total composition prior to mixing with any other composition.

In principal any alkalizing agent is suitable for the purpose of the present invention. Suitable non-limiting examples and preferred ones are the ones according to general structure

$$R_1R_2R_3N$$

wherein $R_1$, $R_2$ and $R_3$ are the same or different H, straight or branched $C_1$ to $C_6$ alkyl, straight or branched $C_1$ to $C_6$ monohydroxy alkyl, straight or branched $C_2$ to $C_6$ polyhydroxyalkyl, carbonate salts such as sodium, potassium and ammonium and bicarbonate salts such as sodium, potassium and ammonium.

Suitable non-limiting examples according to general formula above are ammonia or ammonium hydroxide, 2-aminobutanol, aminoethyl propanediol, aminomethyl propanediol, aminoethyl propanol, aminopropanediol, bishydroxyethyl tromethamine, butyl diethanolamine, butylethanolamine, dibutylethanolamine, diethanolamine, diethylethanolamine, diisopropanolamine, dimethylamino methylpropanol, dimethylisopropanolamine, dimethyl monoethanolamine, ethanolamine, ethyl ethanolamine, isoproanolamine, methylethanolamine, triethanolamine, triisopropanolamine, tromethamine.

More preferred ones are according to the general formula above and among them the preferred ones are ammonia or ammonium hydroxide, aminoethyl propanediol, aminomethyl propanediol, aminoethyl propanol, aminopropanediol, diethanolamine, diethylethanolamine, dimethyl monoethanolamine, ethanolamine, ethyl ethanolamine, isoproanolamine, methylethanolamine, triethanolamine and triisopropanolamine.

Most preferred are ammonia or ammonium hydroxide, diethanolamine, diethylethanolamine, dimethyl monoethanolamine, ethanolamine, ethyl ethanolamine, methylethanolamine, and triethanolamine.

In a preferred from of the invention, composition comprises at least two alkalizing agents. In further preferred embodiment, one of the alkalizing agents is selected from ammonia and/or ammonium hydroxide and carbonate salts such as sodium, potassium and ammonium and bicarbonate salts such as sodium, potassium and ammonium and the second alkalizing agent is selected from compounds according to the above general formula wherein at least one of the $R_1$, $R_2$ and $R_3$ is not H.

Compositions of the present invention are used for hair dressing and preferably as a hair colouring and/or for permanent shaping of hair.

In case of hair colouring, compositions comprise at least one hair dye. The suitable hair dyes are either direct or oxidative dyes. The direct dyes are suitably selected from anionic, cationic and non-ionic ones.

For oxidative dyeing, compositions comprise at least one oxidative dye precursor (developing substance) and optionally at least one coupling substance and further optionally at least one direct dye mentioned above.

With the term oxidative dyeing it is meant that compositions comprise at least one oxidative dye precursor and optionally at least one coupling substance. The term does not mean anything related to the presence of oxidizing agent in the composition.

As a rule, it is possible to incorporate any developing substances known per se. Special mention is made of p-phenylenediamine, p-aminophenol and substituted p-phenylenediamines such as 2,5-diamino-toluene, 2-n-propyl or 2-ethyl-p-phenylenediamine, 2,6-di-methyl-p-phenylene-diamine, 2-(2,5-diaminophenyl)ethanol, 1-amino-4-bis-(2'-hydroxyethyl)amino-benzene, 2-(2-hydroxyethyl amino)-5-aminotoluene, 4,4'-diaminodiphenylamine, 4-aminodiphenylamine, 2-amino-5-N,N-diethyl aminotoluene, 4-amino-N-ethyl-N-isopropyl aniline, 2-chloro-p-phenylenediamine, 1-β-hydroxyethyl-2,5-diamino-4-chlorobenzene, 1-β-hydroxyethyl-2,5-diamino-4-methyl benzene, 2-methoxy-p-phenylenediamine, N,N-diethyl-p-phenylenediamine, 1-amino-4-β-methoxyethyl aminobenzene, 1-dimethylamino-4-aminobenzene, 1-hydroxy-2,5-diamino-4-methyl benzene, 1-hydroxymethyl-2,5-diaminobenzene, 1,3-dimethyl-2,5-diaminobenzene, 1,4-diamino isopropyl benzene and/or 1-amino-4-β-hydroxypropyl aminobenzene, pyrazole and the derivatives thereof such as 1-hydroxyethyl-4,5-diaminopyrazole, 3,4-diamino-5-hydroxypyrazole, 3,5-diaminopyrazole, 3,5-diamino pyrazol-1-carboxamide, 3-amino-5-hydroxypyrazole, 1-phenyl-2-methylpyrazole, 1-phenyl-3-methylpyrazole-5-one, 3,5-dimethylpyrazole, 3,5-dimethylpyrazole-1-methanol, 3,5-diamino-1,2,4-triazole, 4-aminophenol and the derivatives thereof such as 4-amino-3-methylphenol, 2-chloro-4-aminophenol, 2,6-dichloro-4-aminophenol, 2,4-diamino-phenol, 2,6-dibromo-4-aminophenol, tetramino pyrimidines, triaminohydroxy pyrimidines, diaminomono- and -dihydroxy pyrimidines, aminotriazines, 5-amino salicylic acid and/or 1,2,4-triamino benzene or the water-soluble salts thereof.

Further suitable ones aminopyridines are 2,5-diaminopyridine, 2,3-diaminopyridine, 2,6-diaminopyridine, 3-amino-2-methyl amino-6-methoxypyridine, 2-dimethyl-5-aminopyridine, 2-dimethyl aminoethyl-3-hydroxypyridine, 2-amino-4,6-dimethyl pyridine, 2-amino-3-hydroxypyridine, 3-amino-2(β-hydroxyethyl amino)-6-methoxy-pyridine, 2,6-dimethyl amino-5-aminopyridine, 2-di(hydroxyethyl)amino-5-aminopyridine, 2-hydroxyethyl amino-5-aminopyridine, 4-hydroxy-2,5,6-triaminopyrimidine and/or the water-soluble salts thereof.

Within the meaning of the present invention above mentioned developers can as well be present as a mixture of each other.

The total concentration of the dye precursors (developing substances) customarily ranges between 0.001 to 5%, preferably 0.01 to 4% and more preferably 0.05 to 3%, and most preferably 0.1 to 2% by weight, calculated to the total composition, whereby these figures are always related to the proportion of free base.

In a further embodiment of the present invention compositions comprise in addition to at least one oxidative dye precursor at least one coupling substance. As a rule any coupling substance customarily used in oxidative hair colouration area is suitable within the meaning of the present invention. Non-limiting coupling substances, are 5-amino-2-methylphenol, 2-methyl-5-hydroxyethylaminophenol, 2,4,-diamnophenoxyehanol, 2-amino-4-hydroxyethylaminoanisol, 2-methyl-5-amino-6-chlorphenol, 1,3-bis(2,4-diaminophenoxy)propane, 2-bis(2-hydroxyethyl)aminotoluene, 2-amino-5-methylphenol, resorcinol, 2-methyl-resorcinol, 4-chlororesorcinol, 2-amino-4-chlorophenol, 5-amino-4-methoxy-2-methylphenol, 2-aminophenol, 3-amino-phenol, 1-methyl-2-hydroxy-4-aminobenzene, 3-N,N-dimethyl aminophenol, 2,6-dihydroxy-3,5-dimethoxypyridine, 5-amino-3-methylphenol, 6-amino-3-methylphenol, 1,3-diamino-benzene, 1-amino-3-(2'-hydroxyethylamino)benzene, 1-amino-3-[bis(2'-hydroxy-ethyl)amino]benzene, α-naphthol, 4,6-dichlororesorcinol, 1,3-diamino-toluene, 4-hydroxy-1,2-methylenedioxy benzene, 1,5-dihydroxy naphthalene, 1,6-dihydroxy naphthalene, 1,7-dihydroxy naphthalene, 2,7-dihydroxy naphthalene, 1-hydroxy-2-methyl naphthalene, 4-hydroxy-1,2-methyldioxy benzene, 2,4-diamino-3-chlorophenol, 5-amino-2-methoxyphenol and/or 1-methoxy-2-amino-4-(2'-hydroxyethyl amino)benzene or the water-soluble salts thereof. One or more of the above mentioned coupler can also be used in a mixture.

In the hair dyeing compositions according to the invention, the coupling substance(s) as reaction partners of the developing substance(s) are present in approximately the same molecular proportions as the developing substances, i.e. in amounts from 0.001 to 5%, preferably 0.01 to 4% and more preferably 0.05 to 3%, and most preferably 0.1 to 2% by weight, calculated to the total composition, whereby these figures always relate to the proportion of free base.

Further, indole and indoline derivatives of self oxidizing dyestuffs can as well be contained in the colouring composition of the present invention. Examples to those are: 6-aminoindol, 6-hydroxyindole, 1-ethyl-6-hydroxyindole, 1-methyl-4-hydroxyindol, 1-methyl-6-hydroxyindole, 2-methyl-6-hydroxyindole, 5-hydroxyindol, 4-hydroxyindol, 5,6-dihydroxyindole, 6-aminoindoline, 6-hydroxyindoline, 1-ethyl-6-hydroxyindoline, 1-methyl-4-hydroxyindoline, 1-methyl-6-hydroxyindoline, 2-methyl-6-hydroxyindoline, 5-hydroxyindoline, 4-hydroxyindoline, 5,6-dihydroxyindoline and their respective salts.

Compositions comprise at least one direct dye for colouring hair either alone or in mixture with oxidative dyes. Suitable direct dyes are cationic, anionic, neutral dyes and mixtures thereof as available commercially from various suppliers and used mainly in semi-permanent hair colouration.

One of the suitable direct dyes is cationic dyes. Non-limiting examples are Basic Blue 6, Basic Blue 7, Basic Blue 9, Basic Blue 26, Basic Blue 41, Basic Blue 99, Basic Brown 4, Basic Brown 16, Basic Brown 17, Basic Orange 31, Natural Brown 7, Basic Green 1, Basic Red 2, Basic Red 12 Basic Red 22, Basic Red 51, Basic Red 76, Basic Violet 1, Basic Violet 2, Basic Violet 3, Basic Violet 10, Basic Violet 14, Basic Yellow 57 and Basic Yellow 87, and their salts such as chloride, methosulfate, bromide etc. and mixtures thereof.

Further suitable direct dyes are anionic dyes. Suitable non-limiting examples are Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9 and Disperse Violet 1 and their alkali metal salts such as sodium, potassium, and their mixtures.

Further suitable dyes for colouring hair within the meaning of the present invention are those of neutral nitro dyes. Suitable non-limiting examples are HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 11, HC Red No. 13, HC Red No. 54, HC Red No. 14, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15, 2-Amino-6-chloro-4-nitrophenol, picramic acid, 1,2-Diamino-4-nitrobenzol, 1,4-Diamino-2-nitrobenzol, 3-Nitro-4-aminophenol, 1-Hydroxy-2-amino-3-nitrobenzol and 2-hydroxyethylpicramic acid, and their mixtures.

Plant dyestuffs may also be used as hair colorant within the meaning of the present invention for example henna (red or black), alkanna root, laccaic acid, indigo, logwood powder, madder root and rhubarb powder, etc.

It should be noted that the above dyestuffs are also suitable for use in mixture. In other words, cationic, anionic and nitro dyes are used in mixture within the meaning of the present invention. When using direct dyes of various categories, their compatibility must be taken into account.

Among the direct dyes cationic and nitro dyes are preferred ones. Most preferred ones are cationic direct dyes.

Concentration of direct dyes in the compositions of the present invention is within the range of 0.001 to 5%, preferably 0.01 to 4% and more preferably 0.05 to 3%, and most preferably 0.1 to 2% by weight, calculated to total composition.

In further embodiment of the present invention, compositions comprise mixtures of the hair dyes mentioned above. In other words, a hair dyeing composition comprises at least one direct dye and at least one oxidative dye precursor, optionally at least one coupling substance. Direct dyes are here as well selected from cationic, anionic and nitro dyes. Above mentioned concentration for each class of dyestuff are also valid here.

Aqueous compositions of the present invention are used for permanent shaping of hair. Accordingly, permanent shaping compositions according to the invention comprise at least one reducing compound at a concentration of at least 0.5% by weight calculated to total composition. Preferred are thioglycolic acid and thiolactic acid as well as the salts thereof, in particular the ammonium and ethanolamine salts. Further useful thio compounds are in particular cysteine or the hydrochloride thereof, homocysteine, cysteamine, N-acetyl cysteine, thioglycerol, ethanediol monothioglycolate, 1,2-propyleneglycol monothioglycolate (see also WO-A 93/1791), 1,3-propanediol monothioglycolate or the isomer mixture resulting therefrom, 1,3-butanediol and 1,4-butanediol monothioglycolate and the isomer mixtures therefrom, polyethylene glycol, such as di-, tri- and tetraethyleneglycol monothioglycolates, glycerol monothiolactate and further thio acids and the esters thereof, as well as mixtures thereof.

The use of inorganic reducing sulfur compounds such as sodium hydrogen sulfite is basically also possible.

The total reduction agent content in the compositions according to the invention customarily amounts from 0.5 to 15%, preferably 1.0 to 12.5%, more preferably 1.5 to 12.5%, most preferably 2.0 to 12.5% by weight, calculated to total composition as free thioglycolic acid as reference substance.

It should be noted that reducing agents are also used in oxidative colouring composition in order to stabilize oxidative dyeing agents at concentration ranges between 0.2 and 1% by weight, calculated to total composition.

Compositions of the present invention can be in the form of emulsion, solution, dispersion, thickened liquid and/or gel. One or the other forms may be preferred in certain specific applications i.e. emulsions are preferred in case of colouring especially oxidative colouration and solution form especially as a very thin liquid is preferred in case of permanent shaping, especially perming compositions. In case of hair straightening, depending on the used method even very high viscosity emulsions may be preferred.

With the term thickened liquid, it is meant that the compositions comprise additionally a thickening agent.

With the term gel it is meant that the compositions comprise additionally a gelling agent and the gelling agent is a polymer forming a shear thinning gel.

The thickening agents include any polymer either natural or synthetic thickening aqueous composition. Examples are cellulose and its derivatives such as hydroxyethylcellulose, guar and its derivatives such as hydroxypropyl guar. In the selection of the thickening agent compatibility with any other components of the formulation should carefully be examined.

The gelling agents include polymers either synthetic or natural forming shear thinning compositions. Examples to the natural polymers are xanthan gum and its derivatives. Synthetic shear thinning polymers may be those of acrylate polymers commercially available for example under trade name Carbopol. In the selection of the gelling agent compatibility with any other components of the formulation should carefully be examined.

It should be noted that gelling and thickening agents can also be used in mixture. Concentration of the thickening and/or gelling agents should be in the range of 0.05 to 5%, preferably 0.1 to 2.5% by weight calculated to total content.

Compositions of the present invention further comprise at least one surfactant selected from non-ionic, cationic, anionic and amphoteric ones and their mixtures.

As a rule any cationic surfactant is suitable for the compositions of the present invention. With the term cationic surfactant it is meant that the surfactant carries a cationic charge when used in the compositions. In other words, compounds having no cationic charge but when added into the compositions protonate and therewith become cationic are also included within the definition of cationic surfactant. An example to such may be stearyldimethylamine and PEG-2 Cocamine are as a compound not carrying a cationic charge but when used in a composition having acidic pH becomes cationic by protonation.

Preferably at least one cationic surfactant is selected from the compounds with the general formula

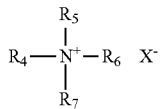

where $R_4$ is a saturated or unsaturated, branched or non-branched alkyl chain with 8-24 C atoms or

where $R_8$ is saturated or unsaturated, branched or non-branched alkyl chain with 7-21 C atoms and n has typical value of 0-4 or

where $R_9$ is saturated or unsaturated, branched or non-branched alkyl chain with 7-21 C atoms and n has typical value of 0-4, and
$R_5$ is a hydrogen, saturated or unsaturated, branched or non-branched alkyl chain with 1-24 C atoms or

where $R_8$ is saturated or unsaturated, branched or non-branched alkyl chain with 7-21 C atoms and n has typical value of 0-4 or

where $R_9$ is saturated or unsaturated, branched or non-branched alkyl chain with 7-21 C atoms and n has typical value of 0-4,
and $R_6$ and $R_7$ are independent from each other H or lower alkyl chain with 1 to 4 carbon atoms which may be substituted with one or two hydroxyl groups or ethoxy or propoxy group with number of ethoxy or propoxy groups varying in the range of 0 to 4, and X is chloride, bromide or methosulfate.

Suitable cationic surfactants are, for example, long-chain quaternary ammonium compounds which can be used alone or in admixture with one another, such as cetyl trimethyl ammonium chloride, myristoyl trimethyl ammonium chloride, behentrimonium chloride, trimethyl cetyl ammonium bromide, stearyl trimethyl ammonium chloride, dimethyl stearyl ammonium chloride, dimethyl dihydrogenated tallow ammonium chloride, stear trimonium chloride, stearamidopropyldimethylamoonium chloride, dipalmitoyl dimonium chloride, distearyl dimethyl ammonium chloride, stearamidopropyl trimonuim chloride.

Further examples to the cationic surfactants are so called esterquats available on the market, for example, under the trade names "Schercoquat®", "Dehyquart®L80" and "Tetranyl®". Still further examples are so called amidoquats again available on the market, for example, under the trade name "INCROQUAT HO" or "OCS".

Suitable non-ionic surfactants are alkyl polyglucosides of the general formula

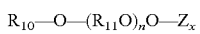

wherein $R_{10}$ is an alkyl group with 8 to 18 carbon atoms, $R_{11}$ is an ethylene or propylene group, Z is a saccharide group with 5 to 6 carbon atoms, n is a number from 0 to 10 and x is a number between 1 and 5. Examples are decyl polyglucoside, cocoyl polyglucoside both are commercially available.

Further nonionic surfactant components are, for example, long-chain fatty acid mono- and dialkanolamides, such as coco fatty acid monoethanolamide and myristic fatty acid monoethanolamide.

Further additionally useful nonionic surfactants are, for example, the various sorbitan esters, such as polyethylene glycol sorbitan stearic acid ester, fatty acid polyglycol esters or poly-condensates of ethyleneoxide and propyleneoxide, as they are on the market, for example, under the trade name "Pluronics®".

Further nonionic surfactants as emulsifiers useful in the compositions according to invention are $C_{10}$-$C_{22}$-fatty alcohol ethoxylates. Especially suited are $C_{10}$-$C_{22}$-fatty alcohol ethers, the alkyl polyglycol ethers known by the generic terms "Laureth", "Myristeth", "Oleth", "Ceteth", "Deceth", "Steareth" and "Ceteareth" according to the CTFA nomenclature, including addition of the number of ethylene oxide molecules, e.g., "Laureth-16":

The average degree of ethoxylation thereby ranges between about 2.5 and about 50, preferably about 10 and about 30.

Among the non-ionic surfactants mentioned above fatty alcohol ethoxylates are the most preferred ones. Above mentioned non-ionic surfactants can also be used as mixture of one category such as several ethoxylated fatty alcohols or several categories such as mixture of alkyl polyglucoside and ethoxylated fatty alcohol.

As further surfactant suitable for the compositions according to the present invention are amphoteric or zwitterionic surfactants. Useful as such are in particular the various known betaines such as alkyl betaines, fatty acid amidoalkyl betaines and sulfobetaines, for example, lauryl hydroxysulfobetaine; long-chain alkyl amino acids, such as cocoaminoacetate, cocoaminopropionate and sodium cocoamphopropionate and -acetate.

Further surfactants suitable within the meaning of the present invention are anionic surfactants of the sulfate, sulfonate, carboxylate and alkyl phosphate type, for example, the known $C_{10}$-$C_{18}$-alkyl sulfates, and in particular the respective ether sulfates, for example, $C_{12}$-$C_{14}$-alkyl ether sulfate, lauryl ether sulfate, especially with 1 to 4 ethylene oxide groups in the molecule, monoglyceride (ether) sulfates, fatty acid amide sulfates obtained by ethoxylation and subsequent sulfatation of fatty acid alkanolamides, and the alkali salts thereof.

Additional anionic surfactants useful are α-olefin sulfonates or the salts thereof, and in particular alkali salts of sulfosuccinic acid semiesters, for example, the disodium salt of monooctyl sulfosuccinate and alkali salts of long-chain monoalkyl ethoxysulfosuccinates.

Suitable surfactants of the carboxylate type are alkyl polyether carboxylic acids and the salts thereof of the formula

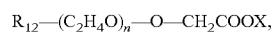

wherein $R_{12}$ is a $C_8$-$C_{20}$-alkyl group, preferably a $C_{12}$-$C_{14}$-alkyl group, n is a number from 1 to 20, preferably 2 to 17, and X is H or preferably a cation of the group sodium, potassium, magnesium and ammonium, which can optionally be hydroxyalkyl-substituted.

Further suitable anionic surfactants are also $C_8$-$C_{22}$-acyl aminocarboxylic acids or the water-soluble salts thereof, such as N-lauroyl glutamate, in particular as sodium salt, as well as, for example, N-lauroyl sarcosinate, N—$C_{12}$-$C_{18}$-acyl asparaginic acid, N-myristoyl sarcosinate, N-oleoyl sarcosinate, N-lauroyl methylalanine, N-lauroyl lysine and N-lauroyl aminopropyl glycine, preferably in form of the water-soluble alkali or ammonium, in particular the sodium salts thereof, preferably in admixture with the above-named anionic surfactants.

Still further anionic surfactants are fatty acid salts, preferably added as a fatty acid and salts formed during preparation of the compositions. Accordingly suitable ones are any fatty acid with 8 to 24 C atoms in its molecule which may be saturated or unsaturated with 1 to 3 ethylenic bonds and branched or straight and can as well be substituted with one or more hydroxyl groups. Suitable non-limiting examples are capric, lauric, myristic, palmitic, oleic, linoleic, stearic, arachidic and behenic acids. Preferred are lauric, myristic, palmitic, oleic and linoleic acids and most preferred is oleic acid.

Total surfactant concentration varies between 0.1 and 20%, preferably 0.5 and 15%, and more preferably 1 to 7.5% by weight calculated to total composition.

Compositions of the present invention can be in the form of emulsion especially oil in water (O/W) emulsion and especially in the case that the compositions are designed for hair colouring purposes. Emulsions according to the present invention preferably comprise at least one fatty alcohol with linear of branched alkyl chain. Suitable ones are fatty alcohols having 12 to 22 C atoms in its alkyl chain. Examples are myristyl alcohol, cetyl alcohol, stearyl alcohol, behenyl alcohol and their mixtures. Preferred are cetyl, stearyl and behenyl alcohol and their mixtures i.e. cetearyl alcohol. Fatty alcohols may be included into the compositions of the present invention at a concentration of 0.1 to 20%, preferably 0.5 to 15% and more preferably 1 to 10% by weight calculated to total composition.

Emulsions should also comprise at least one emulsifier. Suitable emulsifiers are those surfactants mentioned above. Preferred emulsifiers are non-ionic, cationic and anionic surfactant mentioned above. Among the non-ionic surfactant fatty alcohol ethoxylates are the most proffered ones. Among cationic surfactants any cationic surfactant with a single alkyl chain is suitable. Sulfate types of anionic surfactants are the preferred anionic surfactants. The above mentioned concentrations are also suitable for the emulsifiers mentioned here.

Compositions of the present invention can comprise additionally hair conditioning compounds such as oils and/or oily substances, cationic compounds, non-ionic substances. Oils as conditioners according to the present invention are selected from silicone oils either volatile or non-volatile, natural and synthetic oils. Among silicone oils those can be added to the compositions include either volatile or non-volatile dimethicone, dimethiconol, polydimethylsiloxane, DC fluid ranges from Dow Corning, cyclosiloxanes such as DC 245. Synthetic oils include mineral oil such as paraffin oil and petrolatum.

Arylated silicones have been found to be especially suitable for the compositions of the present invention at a concentration range of 0.01 to 5%, preferably 0.05 to 4% more preferably 0.1 to 3% and most preferably 0.1 to 2.5% by weight calculated to total composition prior to mixing with oxidizing lotion. Non-limiting suitable examples are phenyl methicone, phenyl trimethicone, diphenyl dimethicone, diphenylsiloxy phenyl trimethicone, tetramethyl tetraphenyl trisiloxane, triphenyl trimethicone, tetramethly tetraphenyl trisiloxane and trimethyl pentaphenyl trisiloxane.

Particularly preferred arylated silicone is trimethyl pentaphenyl trisiloxane available from Dow Corning under the trade name DC PH-1555 HRI.

It should be noted that compositions of the present invention can also comprise more than one arylated silicone and also in combination with other silicone comprising compounds.

Natural oils suitable are such as olive oil, almond oil, avocado oil, ricinus oil, coconut oil, palm oil, sesame oil, peanut oil, whale oil, sunflower oil, peach kernel oil, wheat germ oil, macadamia nut oil, night primrose oil, jojoba oil, castor oil, or soya oil, lanolin and the derivatives thereof.

Lipophilic oily compounds such as fatty acid esters are also suitable for the composition of the present invention. Examples are such as isopropyl myristate, palmitate, stearate and isostearate, oleyl oleate, isocetyl stearate, hexyl laurate, dibutyl adipate, dioctyl adipate, myristyl myristate, oleyl erucate, cetyl palmitate, etc.

Non-ionic conditioning agents may be polyols such as glycerin, glycol and derivatives, polyethyleneglycoles known with trade names Carbowax PEG from Union Carbide and Polyox WSR range from Amerchol, polyglycerin, polyethyleneglycol mono or di fatty acid esters having general formula

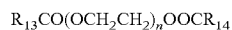

where $R_{13}$ and $R_{14}$ are independent from each other saturated, unsaturated or branched or non-branched alkyl chain with 7 to 21 C atoms and n is typically 2-100.

Composition of the present invention can comprise cationic surfactants according to general formula disclosed above and cationic polymers as conditioning agents. Those are cationic cellulose type polymers know as Polymer JR type from Amerchol such as Polyquaternium 10 or cationic guar gum known with trade name Jaguar from Rhône-Poulenc and chemically for example Guar hydroxypropyl trimonium chloride. Furthermore, chitosan and chitin can also be included in the compositions as cationic natural polymers.

Furthermore, it has especially been found suitable those cationic polymers known with their CTFA category name Polyquaternium. Typical examples of those Polyquaternium 6, Polyquaternium 7, Polyquaternium 10, Polyquaternium 11, Polyquaternium 16, Polyquaternium 22, Polyquaternium 28, Polyquaternium 30, Polyquaternium 37, Polyquaternium 36, Polyquaternium 46, Polyquaternium 67 and Polyquaternium 87.

As well those polymers known with their CTFA category name Quaternium are suitable. Those are for example Quaternium-8, Quaternium-14, Quaternium-15, Quaternium-18, Quaternium-22, Quaternium-24, Quaternium-26, Quaternium-27, Quaternium-30, Quaternium-33, Quaternium-53, Quaternium-60, Quaternium-61, Quaternium-72, Quaternium-78, Quaternium-80, Quaternium-81, Quaternium-82, Quaternium-83 and Quaternium-84.

In this context, reference is also made to the cationic polymers disclosed in DE 25 21 960, 28 11 010, 30 44 738 and 32 17 059, as well as to the products described in EP-A 337 354 on pages 3 to 7. It is also possible to use mixtures of various cationic polymers.

Further cationic polymers are so called aminated silicones such as amodimethicone. The cationic polymers also include the quaternized products of graft polymers from organopolysiloxanes and polyethyl oxazolines described in EP-A 524 612 and EP-A 640 643.

Concentration range for any of the additional conditioners mentioned above is in the range of 0.01 to 10% by weight, preferably 0.05-7.5% by weight, more preferably 0.1-5% by weight calculated to the total composition.

The compositions according to the present invention can also comprise further agents, such as protein hydrolyzates and polypeptides, e.g. keratin hydrolyzates, collagen hydrolyzates of the type "Nutrilan" or elastin hydrolyzates, as well as, in particular vegetable, optionally cationized protein hydrolyzates, for example "Gluadin".

Additional natural plant extracts can as well form part of the compositions of the present invention. Those are incorporated usually in an amount of about 0.01% to about 10%, preferably 0.05% to 7.5%, in particular 0.1% to 5% by weight, calculated as dry residue thereof to the total composition. Suitable aqueous (e.g. steam-distilled) alcoholic or hydro-alcoholic plant extracts known per se are in particular extracts from leaves, fruits, blossoms, roots, rinds or stems of aloe, pineapple, artichoke, arnica, avocado, valerian, bamboo, green tea, blue lotus flower, henbane, birch, stinging nettle, echinacea, ivy, wild angelica, gentian, ferns, pine needles, silver weed, ginseng, broom, oat, rose hip, hamamelis, hay flowers, elderberry, hop, coltsfoot, currants, chamomile, carrots, chestnuts, clover, burr root, cocoanut, cornflower, lime blossom, lily of the valley, marine algae, balm, mistletoe, passion flower, ratanhia, marigold, rosemary, horse chestnut, pink hawthorn, sage, horsetail, yarrow, primrose, nettle, thyme, walnut, wine leaves, white hawthorn, etc.

Suitable trade products are, for example, the various "Extrapone" products and "Herbasol®". Extracts and the preparation thereof are also described in "Hagers Handbuch der pharmazeutischen Praxis", 4$^{th}$ Ed.

The compositions can contain one or more organic solvents such as ethanol, propanol, isopropanol, benzyl alcohol, benzyloxyethanol, alkylene carbonates such as ethylene carbonate and propylene carbonate, phenoxyethanol, butanol, isobutanol, cyclohexane, cyclohexanol, hexyleneglycol, ethylenecarbonate, ethyleneglycol monoethylether, ethylene glycol monobutyl ether, ethylene glycol monophenyl ether, 1-phenylethylalcohol, 2-phenylethylalcohol, o-methoxyphenol.

Concentration of organic solvent can be in the range of 1 to 40%, preferably 1 to 25% by weight, calculated to total composition.

Compositions of the present invention can comprise UV filters for protection of hair from environmental influences such as loss of elasticity, loss of hair colour (bleaching effect of sun light). The UV-absorbing substance is preferably selected from the following compounds: 4-Aminobenzoic acid and the esters and salts thereof, 2-phenyl benzimidazole-5-sulfonic acid and the alkali and amine salts thereof, 4-dimethyl aminobenzoic acid and the esters and salts thereof, cinnamic acid and the esters and salts thereof, 4-methoxycinnamic acid and the esters and salts thereof, salicylic acid and the esters and salts thereof, 2,4-dihydroxybenzophenone, 2,2',4,4'-tetrahydroxy-benzophenone, 2-hydroxy-4-methoxybenzophenone and its 5-sulfonic acid or the sodium salt thereof, 2,2'-dihydroxy-4,4'-dimethoxybenzophenone, 2-hydroxy-5-chlorobenzophenone, 2,2'-dihydroxy-4-methoxybenzophenone, 2,2'-dihydroxy-4,4'-dimethoxy-5,5'-disulfobenzo-phenone or the sodium salt thereof, 2-hydroxy-4-octyloxybenzophenone, 2-hydroxy-4-methoxy-4'-methyl benzophenone, 3-benzyl-idenecampher, 3-(4'-sulfo)-benzylidenebornane-2-one and the salts thereof and/or 3-(4'-methyl benzylidene)-DL-campher, polysilicone-15. The preferred amount of the UV-absorber ranges from about 0.01% to 2.5%, more preferably from 0.05% to 1% by weight, calculated to the total composition.

The compositions of the present invention can comprise one or more hair-restructuring agents. The hair restructuring agents preferred are especially the ones disclosed in the German patent DE 197 51 550 C2. Namely they are ceramide type of compounds, fatty acids and phytosterol or their mixtures.

Preferred ceramide compound is cetyl-PG-hydroxyethylpalmitamide.

Preferred fatty acids are as mentioned above.

Sterols, especially the phytosterols, are as well preferred hair restructuring agents as disclosed in the above mentioned german patent. Especially preferred ones are of plant origin for example ergosterol, sitosterol, stigmasterol, fucosterol, brassicasterol, fungisterol, campesterol, zymosterol, ascosterol, cerevisterol, episterol, faecosterol, spinasterol. Among those phytosterols, the ones found in "Avocadin" which is the unsaponified fraction of the avocado oil is more preferred.

The concentration of ceramide in the compositions of the present invention can be in the range of 0.01 to 2% and especially 0.01 to 1% by weight calculated to the total weight of the composition. The fatty acids may be contained at a level of 0.01 to 2.5% and especially 0.01 to 1% by weight calculated to the total weight of the composition. Phytosterol concentration of the conditioners is less than 1% and preferably in the range of 0.01 to 0.5% by weight calculated to the total weight of the composition. It should be noted without limiting the use of those ingredients the effect of those hair restructuring ingredients is especially elevated when used in combination with penetration enhancers.

Compositions of the present invention may comprise further at least one compound according to the formula

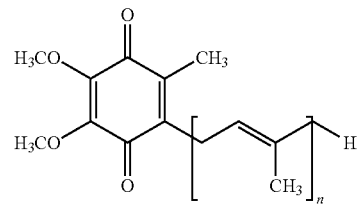

where n is a number from 1 to 10.

The compounds of the above formula are known as Ubiquinone, and also are known as Coenzyme. It should be noted that the compositions of the present invention can certainly comprise more than one ubichinone. Preferred ubichinones are the ones where n is a number between 6 and 10 and especially preferred is Ubichinone 50 where n is 10, also known as Coenzyme Q10. Concentration ubichinone of the above formula in the compositions is from 0.0001 to 1%, preferably from 0.0002 to 0.75%, more preferably from 0.0002 to 0.5% and most preferably from 0.0005 to 0.5% by weight, calculated to total composition.

The pH of the compositions according to the invention is in the range of 2 to 11 preferably 5 to 11, more preferably 6 to 11, most preferably 6.8 to 10. pH of the compositions can be adjusted by using any organic and/or inorganic acids. Composition of the present invention especially in hair colouring area can be used after mixing with an oxidizing agent. The oxidizing agents suitable are hydrogen peroxide, urea peroxide, melamine peroxide or perborate salts. The most preferred is hydrogen peroxide, which is used as a lotion containing 2 to 12% by weight, calculated to composition only comprising hydrogen peroxide.

The new composition as a result of mixing colouring and oxidizing composition allows achieving simultaneous lightening and colouring. The mixing ratio of the colouring composition and oxidizing composition should be in the range of 4:1 to 1:4, by weight, preferably 2:1 to 1:3 by weight.

In case of permanent shaping of hair, oxidizing agents are not mixed with reducing composition but applied after reducing hair and rinsing it off from hair.

Typically, oxidative hair colouring is carried out by mixing two compositions with each other, one being an alkaline composition comprising in addition to the silicone compound and alkalizing agent claimed at least one hair oxidative dye precursor and optionally at least on coupling agent and optionally at least one direct dye, and the other is an acidic composition comprising at least one oxidizing agent, and the resulting composition is applied onto hair and after processing at a temperature in the range of 20 to 40° C. for 5 to 45 min it is rinsed off from hair.

In case that the composition comprise only direct dyes, colouring can be carried out without mixing with a composition comprising oxidizing agent in the same way as described above paragraph. In an alternative way and when lightning and colouring is at the same time targeted, than composition of the present invention comprising only one or more direct dyes is mixed with a composition comprising at least one oxidizing agent and further colouration is carried out as described above.

It is certainly possible to use composition of the present invention only for hair colour lightning wherein composition of the present invention is mixed with an oxidizing agent and applied onto hair and after processing for certain time, rinsed off from hair.

Perming is carried out by applying a composition according to present invention and further comprising at least one reducing agent onto shampooed and towel dried hair which is washed and is wound on curlers, and after processing of 1 to 25 min at a temperature in the range of 20 to 45° C., rinsed off from hair and hair is optionally treated with an acidic composition and without rinsing off a composition comprising at least one oxidizing agent is applied onto hair and curlers are removed from hair and hair is optionally rinsed off after processing of 1 to 15 min at room temperature.

Furthermore, compositions of the present invention can comprise all substances customarily found in such preparations. Examples of such substances are complexing agents, preservatives, fragrances, etc.

Following examples are to illustrate the invention but not to limit.

EXAMPLE 1

|  | % by weight |
| --- | --- |
| Dow Corning HMW 2220 | 1.0 |
| Monoethanolamine | q.s. to pH 9.5 |
| Fragrance, preservative | q.s. |
| Water | q.s. to 100 |

Above composition was applied onto hair after mixing at a weight ratio of 1:1 with a composition comprising 6% by weight hydrogen peroxide (the resulting composition had a pH of approximately 9.0) and was processed for 10 min and afterwards rinsed off from hair. The hair was excellently lightened and had shiny attractive appearance and easily combable. Exclusion of silicone copolymer resulted in uncared appearance and the hair was difficult to comb.

The above composition was very thin and therefore was dripping off from hair. In order to prevent this 0.5% hydroxyethylcellulose was dissolved in the compositions and with the resulting composition hair was lightened much more homogeneously and shiny appearance was homogeneous as well. In subsequent trials in this example 0.5% hydroxyethylcellulose comprising composition was used.

Further, the above composition was added 0.5% Basic red 51 and directly applied onto hair and rinsed off from hair after processing of 5 min at ambient temperature. Excellent red shine was observed and such result was not possible to achieve in the absence of silicone copolymer.

Additionally the composition comprising Basic red 51 was mixed with a composition comprising 6% by weight hydrogen peroxide at a weight ratio of 1:1 and applied onto hair. Hair was excellently lightened, had excellent red shine, and had good combability. Exclusion of silicone copolymer resulted in loss of combability and shine was reduced as well.

Further, into the above composition 0.5% para-toluenediamine and 0.3% resorcinol was added and the composition was mixed with a composition comprising 6% by weight hydrogen peroxide (the resulting composition had a pH of approximately 9.0) and was processed for 30 min and afterwards rinsed off from hair. The hair was coloured into matt brown and had attractive appearance and easily combable. Exclusion of silicone copolymer resulted in uncared appearance and the hair was difficult to comb.

In a further trial, oxidative dye precursor and coupler comprising composition given above, 0.05% by weight basic red 51 was dissolved and the resulting composition was mixed with a composition comprising 6% by weight hydrogen peroxide (the resulting composition had a pH of approximately 9.0) and was processed for 30 min and afterwards rinsed off from hair. The hair was coloured into reddish brown and had shiny attractive appearance and easily combable. Exclusion of silicone copolymer resulted in uncared appearance and the hair was difficult to comb.

The above composition without thickening agent was used for perming hair after adding 10% by weight of ammonium thioglycolate. The composition was applied onto freshly shampoo and towel dried hair after wounding hair on curlers. After processing of approximately 15 min at approximately 40° C. the composition was rinsed off from hair and towel dried and an oxidizing composition comprising 2% hydrogen peroxide and having pH 4.0 is applied onto hair and after 5 min of processing the curler were removed and after additional 5 min processing hair was rinsed off with water. Excellent homogeneously curled hair was obtained with nice shine and excellent combability. Exclusion of silicone copolymer resulted in inhomogeneous curls and less shiny and difficult to comb hair. Additionally hair had as a whole smooth surface so that had less fly-aways and had excellent elasticity.

The above process was repeated on a damage hair wherein after rinsing off the reducing agent hair was treated with a composition comprising as well silicone copolymer and having pH 3.0 and oxidized afterwards in the same as described above. Curl efficiency, shiny appearance of hair and combability was further improved. Elasticity was improved further and hair had less flyaway.

EXAMPLE 2

|  | % by weight |
| --- | --- |
| Cetearyl alcohol | 10.0 |
| Cocamide MEA | 4.0 |
| Sodium lauryl sulphate | 1.5 |
| Propylene glycol | 2.0 |
| Dow Corning HMW 2220 | 1.0 |
| 2,5-Diaminotoluene sulphate | 0.55 |
| 4-Chlorresorcinol | 0.17 |
| Resorcinol | 0.05 |
| 3-Aminophenol | 0.03 |
| Sodium sulfite | 1.0 |
| Monoethanolamine | q.s. to pH 10.0 |
| Fragrance, preservative | q.s. |
| Water | to 100 |

For comparative purposes the same composition was produced but not comprising Dow Corning HMW 2220.

The above composition was tested in a half side test against the comparative composition with 10 consumers having shoulder length hair. The above composition was mixed with a composition comprising 6% hydrogen peroxide at a weight ratio of 1 to 1 and applied onto hair and processed for 30 min at a temperature of 40° C. and rinsed off. Comments from the consumer were the side coloured with the inventive composition felt soft and combable and the colour achieved with the inventive composition had significantly more shine, brilliance and vibrancy than the side treated with the comparative composition. 8 volunteers preferred the side according to the invention and 2 could not see any difference.

EXAMPLE 3

| | % by weight |
|---|---|
| Cetearyl alcohol | 10.0 |
| Cocamide MEA | 4.0 |
| Sodium lauryl sulphate | 1.5 |
| Propylene glycol | 2.0 |
| Dow Corning HMW 2220 | 0.9 |
| 2,5,6-Triamino-4-hydroxypyrimidin sulphate | 1.05 |
| 4-amino-hydroxytoluene | 0.55 |
| Basic red 51 | 0.10 |
| Acid red 52 | 0.05 |
| Sodium sulfite | 1.0 |
| Monoethanolamine | q.s. to pH 10.0 |
| Fragrance, preservative | q.s. |
| Water | to 100 |

Similar results were observed as in example 2.

EXAMPLE 4

| | % by weight |
|---|---|
| Cetearyl alcohol | 10.0 |
| Cocamide MEA | 4.0 |
| Sodium lauryl sulphate | 1.5 |
| Propylene glycol | 2.0 |
| Dow Corning HMW 2220 | 1.0 |
| Phenyl trimethicone | 0.2 |
| 2,5-Diaminotoluene sulphate | 0.43 |
| HC Yellow 5 | 0.10 |
| 4-amino hydroxytoluene | 0.02 |
| Resorcinol | 0.10 |
| m-aminophenol | 0.07 |
| Sodium sulfite | 1.0 |
| Ammonium hydrogen carbonate | 1.5 |
| Monoethanolamine | q.s. to pH 10.0 |
| Fragrance, preservative | q.s. |
| Water | to 100 |

Similar results were observed as in Example 2.

EXAMPLE 5

| | % by weight |
|---|---|
| Cetearyl alcohol | 10.0 |
| Cocamide MEA | 4.0 |
| Sodium lauryl sulphate | 1.5 |
| Propylene glycol | 2.0 |
| Dow Corning HMW 2220 | 1.0 |
| Trimethyl pentaphenyl trisiloxane | 0.5 |
| 2,5,6-Triamino-4-hydroxypyrimidine sulphate | 0.01 |
| 2,5-Diaminotoluene sulphate | 0.55 |
| 4-Chlorresorcinol | 0.17 |
| Basic red 51 | 0.02 |
| Resorcin | 0.05 |
| 3-Aminophenol | 0.03 |
| Sodium sulfite | 1.0 |
| Monoethanolamine | q.s. to pH 10.0 |
| Fragrance, preservative | q.s. |
| Water | to 100 |

Similar results were observed as in the Example 2

EXAMPLE 6

| | | |
|---|---|---|
| Ammonium thioglycolate (60%) | 21.3 | (% by wt.) |
| Ammonium hydrogen carbonate | 5.0 | |
| 1,3-butylene gylcol | 3.0 | |
| Dow Corning HMW 2220 | 1.0 | |
| PEG-40-Hydrogenated castor oil | 0.7 | |
| Perfume | 0.4 | |
| Ammonia, 25% | ad pH 8.3 | |
| Water | ad 100.0 | |

With this composition the hair was permanently waved for about 15 minutes, rinsed and neutralized for about 8 minutes with a customary 2.5% $H_2O_2$ composition. Homogeneous wave appearance was obtained. Exclusion of Dow Corning HMW 2220 resulted in less homogeneous perm appearance.

EXAMPLE 7

| | | |
|---|---|---|
| Ammonium thioglycolate (60%) | 20 | (% by wt.) |
| Ammonium hydrogen carbonate | 4.0 | |
| 1,3-butylene gylcol | 3.0 | |
| Dow Corning HMW 2220 | 1.0 | |
| PEG-40-Hydrogenated castor oil | 0.7 | |
| Perfume | 0.4 | |
| Ammonia, 25% | ad pH 8.3 | |
| Water | ad 100.0 | |

With this composition the hair was permanently waved for about 15 minutes, rinsed and neutralized for about 8 minutes with a customary 2.5% $H_2O_2$ composition. Homogeneous wave appearance was obtained. Exclusion of Dow Corning HMW 2220 resulted in less homogeneous perm appearance.

EXAMPLE 8

| | | |
|---|---|---|
| Ammonium thioglycolate (60%) | 15.0 | (% by wt.) |
| Ammonium hydrogen carbonate | 2.5 | |
| Ceteth-20 | 0.7 | |
| Cetrimonium chloride | 0.1 | |
| Dow Corning HMW 2220 | 1.0 | |
| 1,3-butylene gylcol | 0.5 | |
| Perfume | 0.4 | |

| | |
|---|---|
| Ammonia, 25% | ad pH 8.0 |
| Water | ad 100.0 |

The permanent wave achieved with this composition was similar to the one obtained with the composition according to Example 6.

Exclusion of Dow Corning HMW 2220 led to waves with substantially weaker contours.

EXAMPLE 9

| | | |
|---|---|---|
| Ammonium thioglycolate (60%) | 0.9 | (% by wt.) |
| Cystein hydrochloride | 5.7 | |
| Ammonium hydrogen carbonate | 1.5 | |
| Acetylcystein | 0.7 | |
| Cetrimonium chloride | 0.1 | |
| 1,3-butylene gylcol | 0.5 | |
| Dow Corning HMW 2220 | 1.0 | |
| Amodimethicone | 0.2 | |
| Coenzyme Q10 | 0.05 | |
| Oleic acid | 0.05 | |
| Perfume | 0.4 | |
| Ammonia, 25% | ad pH 9.8 | |
| Water | ad 100.0 | |

The permanent wave achieved with this composition was similar to the one obtained with the composition according to Example 1.

Exclusion of Dow Corning HMW 2220 led to substantially weaker waves.

EXAMPLE 10

A permanent waving product consisting of two Compositions A and B, filled into a two-chamber packaging the chambers of which were kept separate until application, was prepared by destruction of the separating wall and applied onto human hair rolled onto curlers. The hair was rinsed after about fifteen minutes processing and neutralized for about five minutes with a 2.5% $H_2O_2$ neutralizer composition, rinsed again, shampooed and dried.

An expressive, even, intensive permanent wave was obtained.

An identical treatment which had no Dow Corning HMW 2220 showed a visibly inferior wave.

Composition A:

| | | |
|---|---|---|
| Ammonium hydrogen carbonate | 4.5 | (g) |
| Dow Corning HMW 2220 | 1.2 | |
| PEG-65-Hydrogenated castor oil | 0.8 | |
| Isopropyl alcohol | 1.5 | |
| Ethoxydiglycol | 2.0 | |
| Cocoamidopropyl betaine | 1.0 | |
| Perfume | 0.3 | |
| Coenzyme Q10 | 0.05 | |
| Turbidifying agent | 0.5 | |
| Ammonia, 25% | ad pH 8.4 | |
| Water | ad 72.0 | |

Composition B:

| | | |
|---|---|---|
| Ammonium thioglycolate, 70% | 18.0 | (g) |
| Thiolactic acid | 2.0 | |
| 2-Methyl-1.3-propanediol | 0.5 | |
| Ammonia, 25% | ad pH 5.5 | |
| Water | ad 28.0 | |

After mixing of both Compositions a ready-to-use product with a pH-value of 7.4 was obtained.

EXAMPLE 11

A permanent waving product filled into a two-chamber package was prepared in analogy to Example 10.

Composition A:

| | | |
|---|---|---|
| Ammonium hydrogen carbonate | 3.5 | (g) |
| Dow Corning HMW 2220 | 0.8 | |
| Ethanol | 0.5 | |
| 1-Methoxypropanol | 1.0 | |
| Cocoamidopropyl betaine | 1.0 | |
| PEG-25-glyceryl cocoate | 0.8 | |
| Coenzyme Q10 | 0.1 | |
| Polyquaternium-6 | 0.05 | |
| Oleic acid | 0.05 | |
| Perfume | 0.3 | |
| Turbidifying agent | 0.5 | |
| Ammonia, 25% | ad pH 8.3 | |
| Water | ad 72.0 | |

Composition B:

| | | |
|---|---|---|
| Ammonium thioglycolate, 70% | 13.0 | (g) |
| Thiolactic acid | 0.5 | |
| 2-Methyl-1,3-propanediol | 1.5 | |
| Ammonia, 25% | ad pH 5.5 | |
| Water | ad 28.0 | |

A product with a pH-value of 7.4 was obtained by admixture of the Compositions immediately prior to application. After application onto dyed hair this mixture resulted in an expressive permanent wave, which had no effect whatever on the color gloss and color intensity.

EXAMPLE 12

Alkaline Permanent Waving Gel

| | | |
|---|---|---|
| Ammonium thioglycolate, 70% | 15.0 | (g) |
| Ammonium hydrogen carbonate | 4.5 | |
| PEG-40-Hydrogenated castor oil | 0.7 | |
| $C_{12}$-$C_{18}$-Fatty alcohol mixture | 3.5 | |
| Cetrimonium chloride | 1.0 | |
| Dow Corning HMW 2220 | 0.6 | |
| Amodimethicone | 0.05 | |
| 2-Methyl-1,3-propanediol | 0.5 | |
| Coenzyme Q10 | 0.1 | |
| Perfume | 0.3 | |
| Ammonia, 25% | ad pH 8.0 | |
| Water | ad 100.0 | |

Intermediate Treatment Composition

| | |
|---|---|
| Asparagic acid | 0.25 % by weight |
| Glutamic acid | 0.50 |
| Alanin DL | 0.25 |
| Magnesium sulfate | 10.00 |
| Dow Corning HMW 2220 | 0.25 |
| Cetrimonium chloride | 0.25 |
| Water | q.s. to 100 |

The above composition had a pH of 4.10.

EXAMPLE 13

Straightening Composition

| | |
|---|---|
| Thioglycolic acid | 8.0 (% by wt.) |
| $C_{16}$-$C_{22}$-Fatty alcohol mixture | 3.5 |
| Oleth-50 | 2.5 |
| Laureth-23 | 1.5 |
| Dow Corning HMW 2220 | 1.0 |
| Cetrimonium chloride | 1.0 |
| Ethanol | 5.0 |
| Perfume | 0.6 |
| Monoethanolamine | ad pH 9.3 |
| Water | ad 100.0 |

This composition constitutes an effecting smoothing composition for kinky hair.

The invention claimed is:

1. An aqueous composition for hair wherein it comprises at least one alkalizing agent and an aqueous emulsion of divinyldimethicone/dimethicone copolymer with an internal phase viscosity of more than $1 \times 10^8$ mm$^2$/s measured at 0.01 Hz and at about 25° C.

2. The composition according to claim 1 wherein aqueous emulsion of divinyldimethicone/dimethicone copolymer has an internal phase viscosity of more than $1.1 \times 10^8$ mm$^2$/s, measured at 0.01 Hz and at about 25° C. and present in the compositions at a concentration of 0.01 to 5% calculated to total composition prior to mixing with any other composition.

3. The composition according to claim 1, wherein at least one alkalizing agent is selected from compounds according to general structure $$R_1R_2R_3N$$

wherein $R_1$, $R_2$ and $R_3$ are the same or different H, straight or branched $C_1$ to $C_6$ alkyl, straight or branched $C_1$ to $C_6$ monohydroxy alkyl, straight or branched $C_2$ to $C_6$ polyhydroxyalkyl, ammonium carbonate and salts thereof, at a total concentration of 0.1 to 30% by weight calculated to total composition prior to mixing with any other composition.

4. The composition according to claim 1, wherein it comprises at least two alkalizing agents, wherein the first alkalizing agent is at least one compound selected from ammonia, ammonium hydroxide, ammonium carbonate and salts thereof and the second alkalizing agent is selected from compounds according to the above general formula wherein at least one of the $R_1$, $R_2$ and $R_3$ is not H.

5. The composition according to claim 1, wherein it comprises at least one oxidative dye precursor, optionally at least one coupling compound.

6. The composition according to claim 1, wherein it comprises at least one direct dye selected from cationic, anionic and nitro dyes.

7. The composition according to claim 1, wherein it comprises at least one reducing agent.

8. The composition according to claim 1, wherein it comprises at least one surfactant selected from non-ionic, cationic, anionic and amphoteric surfactants.

9. The composition according to claim 1, wherein at least one conditioning agent selected from compounds according to general formula $$R_4-\overset{\overset{R_5}{|}}{\underset{\underset{R_7}{|}}{N^+}}-R_6 \quad X^-$$

where $R_4$ is a saturated or unsaturated, branched or non-branched alkyl chain with 8-24 C atoms or $$R_8CONH(CH_2)_n$$

where $R_8$ is saturated or unsaturated, branched or non-branched alkyl chain with 7-21 C atoms and n has typical value of 0-4 or $$R_9COO(CH_2)_n$$

where $R_9$ is saturated or unsaturated, branched or non-branched alkyl chain with 7-21 C atoms and n has typical value of 0-4, and $R_5$ is a hydrogen, saturated or unsaturated, branched or non-branched alkyl chain with 1-24 C atoms or $$R_8CONH(CH_2)_n$$

where $R_8$ is saturated or unsaturated, branched or non-branched alkyl chain with 7-21 C atoms and n has typical value of 0-4 or $$R_9COO(CH_2)_n$$

where $R_9$ is saturated or unsaturated, branched or non-branched alkyl chain with 7-21 C atoms and n has typical value of 0-4, and $R_6$ and $R_7$ are independent from each other H or lower alkyl chain with 1 to 4 carbon atoms which may be substituted with one or two hydroxyl groups or ethoxy or propoxy group with number of ethoxy or propoxy groups varying in the range of 0 to 4, and X is chloride, bromide or methosulfate, oils, oily substances, cationic polymers and non-ionic compounds.

10. The composition according to claim 6 wherein it further comprises at least one fatty alcohol.

11. The composition according to claim 1, wherein it further comprises one or more organic solvent(s).

12. The composition according to claim 1, wherein it further comprises at least one compound according to the formula where n is a number from 1 to 10 and/or at least one UV filter.

13. The composition according to claim 1, wherein it comprises at least one compound selected from protein hydrolysates, polypeptides, natural plant extracts, ceramides and/or pseudoceramides, phytosterols, and fatty acids.

14. The composition according to claim 1, wherein it has a pH between 2 and 11.

15. A process for treating hair according to one of the processes selected from a to e, wherein
   a—oxidative hair colouring is carried out by mixing two compositions with each other, one being a composition according to claim 1, comprising additionally at least one hair oxidative dye precursor and optionally at least on coupling agent and optionally at least one direct dye, and the other is an acidic composition comprising at least one oxidizing agent, and the resulting composition is applied onto hair and after processing at a temperature in the range of 20 to 40° C. for 5 to 45 min it is rinsed off from hair,
   b—colouring is carried out by applying a composition according to claim 1, comprising additionally at least one direct dye onto hair and after processing at a temperature in the range of 20 to 40° C. for 5 to 45 min it is rinsed off from hair,
   c—colouring is carried out by applying a composition according to claim 1 comprising additionally at least one direct dye onto hair after mixing with a composition comprising at least one oxidizing agent and after processing at a temperature in the range of 20 to 40° C. for 5 to 45 min it is rinsed off from hair,
   d—composition according to claim 1 is applied onto hair after mixing with a composition comprising at least one oxidizing agent and after processing at a temperature in the range of 20 to 40° C. for 5 to 45 min it is rinsed off from hair,
   e—perming is carried out by applying a composition according to claim 1, and further comprising at least one reducing agent onto shampooed and towel dried hair which is washed and is wound on curlers, and after processing of 1 to 25 min at a temperature in the range of 20 to 45° C., rinsed off from hair and hair is optionally treated with an acidic composition and without rinsing off a composition comprising at least one oxidizing agent is applied onto hair and curlers are removed from hair and hair is optionally rinsed off after processing of 1 to 15 min at room temperature.

* * * * *